United States Patent
Fleiszig et al.

(10) Patent No.: US 6,984,622 B2
(45) Date of Patent: Jan. 10, 2006

(54) USE OF LIPOPOLYSACCHARIDES TO MANAGE CORNEAL INFECTIONS AND WOUNDS

(75) Inventors: Suzanne M. J. Fleiszig, Oakland, CA (US); Nancy A. McNamara, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 484 days.

(21) Appl. No.: 10/121,227

(22) Filed: Apr. 10, 2002

(65) Prior Publication Data

US 2002/0110553 A1 Aug. 15, 2002

Related U.S. Application Data

(63) Continuation of application No. 09/275,724, filed on Mar. 24, 1999, now abandoned.
(60) Provisional application No. 60/079,293, filed on Mar. 25, 1998.

(51) Int. Cl.
*A61K 38/00* (2006.01)

(52) U.S. Cl. .............................. 514/2; 514/12
(58) Field of Classification Search ............ 514/2, 514/12; 424/405; 530/300, 324
See application file for complete search history.

(56) References Cited

U.S. PATENT DOCUMENTS

| | | | | |
|---|---|---|---|---|
| 5,242,902 A | * | 9/1993 | Murphy et al. | 514/12 |
| 5,549,894 A | * | 8/1996 | Hunt | 424/94.64 |
| 5,766,624 A | * | 6/1998 | Janoff et al. | 424/450 |
| 5,972,594 A | * | 10/1999 | Heine | 435/4 |
| 6,043,220 A | * | 3/2000 | Chang et al. | 514/12 |
| 6,143,498 A | * | 11/2000 | Olsen et al. | 435/6 |
| 6,159,936 A | * | 12/2000 | Lehrer et al. | 514/13 |
| 6,329,340 B1 | * | 12/2001 | Bougueleret et al. | 514/12 |
| 6,545,140 B1 | * | 4/2003 | Harmon et al. | 536/23.5 |
| 2002/0037260 A1 | * | 3/2002 | Budny et al. | 424/49 |
| 2002/0076393 A1 | * | 6/2002 | Fehlbaum et al. | 424/85.1 |
| 2002/0147301 A1 | * | 10/2002 | Lehrer et al. | 530/324 |
| 2003/0100483 A1 | * | 5/2003 | Lehrer et al. | 514/2 |
| 2003/0235577 A1 | * | 12/2003 | Shapiro et al. | 424/94.65 |

OTHER PUBLICATIONS

McNamara N. Peptide Antibiotic Messenger RNA Expressed by Human Corneal Epithelium. IOVS 39(4) 665, abstract 3071, Mar. 15, 1998.*

Haynes R. Innate Defence of the Eye by Antimicrobial Defensin Peptides. Lancet 352(9126)451–2, Aug. 8, 1998.*

Bartels et al., *Nature*, vol. 387 p. 861, Jun. 16, 1997.*

Fulton et al., *The Lancet*, vol. 350, pp. 1750–1751, Dec. 13, 1997.*

Iromm et al., *Eur. J. Biochem.*, vol. 237, pp. 86–92, 1996.*

\* cited by examiner

*Primary Examiner*—Ralph Gitomer
(74) *Attorney, Agent, or Firm*—Fish & Richardson P.C.

(57) ABSTRACT

The antibiotic polypeptide β-defensin-2 (hBD-2) is expressed in the eye, and is useful for treating ocular wounds. hBD-2 is increased in the eye upon exposure to lipopolysaccharides (LPS). Administration of LPS to the eye thereby provides a useful method for increasing the amount of this antibiotic peptide in the eye.

4 Claims, No Drawings

USE OF LIPOPOLYSACCHARIDES TO MANAGE CORNEAL INFECTIONS AND WOUNDS

CROSS REFERENCE TO RELATED APPLICATIONS

This application is a continuation of U.S. patent application Ser. No.: 09/275,724, filed Mar. 24, 1999; now abandoned which claims priority to U.S. Provisional Application No.: 60/079,293, filed Mar. 25, 1998. All applications are incorporated herein by reference.

STATEMENT AS TO FEDERALLY SPONSORED RESEARCH

The work resulting in this invention was supported in part by the National Institutes of Health-National Eye Institute, R01 EY-11221-02. The U.S. Government may be entitled to certain rights in the invention.

BACKGROUND OF THE INVENTION

Approximately 24 million Americans wear soft contact lenses, and clinical studies have demonstrated that overnight use (extended wear) of these lenses is a significant risk factor for corneal infection, which can result in permanent vision loss (Buehler, P., et al., *Arch Ophthalmol.* 110:1555–1558, 1992; Wilhelmus, K., *CLAO J* 13:211–214, 1987). The defenses that normally protect the eye against infection are not well understood.

The most common pathogen involved in contact lens-associated corneal infection is *Pseudomonas aeruginosa*. To cause corneal infection in vivo, *P. aeruginosa* must bind to the epithelial cell surface; however, before binding can occur the pathogen must resist nonspecific ocular immune mechanisms that help to prevent infection under normal conditions. These include the presence of components with antibacterial properties in the tear film (e.g., lysozyme, lactoferrin, peroxidase, ceruloplasmin, prealbumin, sialin, β-lysin, and cytokines), as well as the sheering force of the blink which wipes the ocular surface, enhances the flow of tears, and facilitates removal of unwanted pathogens from the eye. Furthermore, the innermost layer of the human tear film contains mucus, a glycoprotein gel that serves to improve the spread and stability of aqueous tears, lubricate and protect the underlying corneal epithelium (Holly, F., and Lemp, M., *Exp Eye Res* 11:239–250, 1971). Research has shown that antibacterial tear film components are not fully effective against *P. aeruginosa*, however it has been demonstrated that in the open blinking eye, mucins can bind *P. aeruginosa* and may thereby facilitate bacterial clearance from the ocular surface via normal tear exchange (Fleiszig, S., et al., *Infect. Immun.* 62:1799–1804, 1994). This mechanical clearance mechanism, however, does not explain why the ocular surface is not normally heavily colonized by bacteria as is the case for other mucous membranes.

After contact with microorganisms, animal studies have shown that Xenopus skin (Zasloff, M., *Proc. Natl. Acad. Sci.* 84:5449–5453, 1987), and bovine trachea and tongue epithelia (Schonwetter, B., et al., *Science* 267:1645–1648, 1995) are rich in sources of peptide antibiotics (Boman, H., *Annu. Rev. Immunol.* 13:61–92, 1995), which could be involved in the unexpected resistance of these tissues to infection. Broad spectrum antimicrobial substances have been demonstrated at several body surfaces that act rapidly to neutralize a broad range of potential pathogenic microbes.

One type of antimicrobial substances are the defensins. In general, defensins are characterized as cationic antimicrobial peptides that are generally less than 50 amino acids long, and contain three pairs of disulfide linked cysteines. Three types of defensin polypeptides are known: the classical defensins, the β-defensins, and the insect defensins (see Martin, E., et al., "Defensins and other endogenous peptide antibiotics of vertebrates," *J. Leukocyte Biol.* 58:128–133, 1995; Ganz, T., and Lehrer, R. I., "Defensins," *Curr. Opinion Immunol.* 6:584–589, 1994, both incorporated herein by reference).

Classical defensins form a triple-stranded β-sheet structure connected by a loop with a β-hairpin hydrophobic finger, and are expressed in granules of myeloid cells such as neutrophils. The β-defensins are cationic peptides with amphiphilic anti-parallel beta sheet structures. The β-defensins differ from classical defensins in the location and connectivity of their conserved cysteines and other conserved amino acids, such as glycine and proline. A human β-defensin (hBD-1) was found to be produced by the urogenital tract epithelia and, to a lesser extent, trachea and lung epithelia (Zhoa, C., et al, *FEBS Lett.* 396:319–322, 1996). The expression of human β-defensin-1 does not appear to be regulated by the presence of bacteria or inflammatory stimuli (Bensch, K., et al., *FEBS Lett.* 368:331–335, 1995; Zhoa 1996, supra).

More recently, Harder, J., et al (*Nature* 387:861, 1997, incorporated herein by reference) showed that human skin expresses an inducible, transcriptionally regulated, antibiotic peptide, which shows homology to bovine tongue- and trachea-derived antimicrobial peptides (Schonwetter et al. 1995, supra). This peptide is characterized by an amphiphilic beta sheet that is believed to bind strongly to target bacteria, insert into the microbial lipid membrane, and thereby alter membrane permeability and internal homeostasis. The peptide, named human β-defensin-2, is the second human β-defensin to be described. Unlike hBD-1, human β-defensin-2 (hBD-2) is regulated at a transcriptional level in response to contact with microorganisms or TNFα, and is effective in killing the gram-negative bacteria *P. aeruginosa* and *Escherichia coli*, and the yeast *Candida albicans*.

SUMMARY OF THE INVENTION

One aspect of the invention is a method for treating wounds in mammalian ocular tissue to promote healing by applying a therapeutically effective amount of a β-defensin-2 polypeptide to the wound.

Another aspect of the invention is a method for treating a subject having or at risk of having a corneal infection, by administering a therapeutically effective amount of a β-defensin-2 polypeptide.

Another aspect of the invention is a method for identifying a compound which modulates the expression of a β-defensin-2 in the cornea by incubating ocular epithelial cells with the compound, and determining the effect of the compound on the expression or activity of β-defensin.

Another aspect of the invention is a method of treating a subject having or at risk of having a corneal wound or corneal infection by introducing into a cell of the subject a nucleotide sequence encoding a β-defensin-2 polypeptide under the control of a eukaryotic promoting sequence, such that the cell is genetically transformed and expresses the β-defensin-2 polypeptide.

Another aspect of the invention is a method of treating a subject having or at risk of having a corneal wound or corneal infection by administering to the subject a therapeutically effective amount of a compound which induces the expression of β-defensin-2.

Another aspect of the invention is a composition for administering a β-defensin-2 polypeptide to a subject having or at risk of having a corneal wound or corneal infection comprising a therapeutically effective amount of a β-defensin-2 polypeptide in a pharmaceutically acceptable carrier.

One advantage of the invention is that the β-defensin-2 polypeptides can be used as a tear film supplement that can be used in conjunction with contact lens wear to prevent bacterial infection. No such tear film supplements are currently available.

An advantage of the invention is that β-defensin antimicrobial peptides such as β-defensin-2 are naturally occurring antibiotics. The risk of complications and/or adverse reactions associated with a synthetic antimicrobial treatment regimen is therefore substantially reduced. A further advantage of the invention is that microorganisms are less likely to develop resistance to a naturally occurring β-defensin antimicrobial polypeptide as compared to a synthetic antimicrobial therapeutic agents.

Contact lens wear or some other predisposing factor may alter the expression of a β-defensin, thus tear film supplements containing a β-defensin have the advantage of restoring the normal environment of the eye, and thus may help to further prevent corneal infection.

A further advantage is that the use of an endogenous peptide antibiotics like avoids the problems of acquired resistance of the subject that commonly occur with the use of synthetic antimicrobial therapeutic agents.

DESCRIPTION OF THE PREFERRED EMBODIMENTS

The present invention is based on the finding that the β-defensins can be used to treat wounds, specifically to treat corneal wounds by preventing infection. A "classical defensin" is an anti-microbial polypeptide which forms a triple-stranded β-sheet structure connected by a loop with a β-hairpin hydrophobic finger (see Martin, E., et al., "Defensins and other endogenous peptide antibiotics of vertebrates," *J. Leukocyte Biol.* 58:128–133, 1995; Ganz, T., and Lehrer, R. I., "Defensins," *Curr. Opinion Immunol.* 6:584–589, 1994, both incorporated herein by reference). Classical defensins are expressed in granules of cells such as neutrophils. A "β-defensin" is a cationic anti-microbial peptide having amphiphilic anti-parallel beta sheet structures. The β-defensins differ from classical defensins in the location and connectivity of their conserved cysteines and other conserved amino acids, such as glycine and proline.

The β-defensins include tracheal antimicrobial peptide, lingual antimicrobial peptide, bovine neutrophil beta defensin, gallinacin, turkey heterophil peptide, human β-defensin-1 (hBD-1), and human β-defensin-2 (hBD-2). Preferably, the β-defensin is a β-defensin that is expressed in epithelium (e.g., tracheal antimicrobial peptide, lingual antimicrobial peptide, and human β-defensin-1 and human β-defensin-2). More preferably, the β-defensin is human β-defensin-2 (hBD-2). Without being bound by theory, it is believed that a β-defensin binds strongly to target bacteria, and inserts into the microbial lipid membrane, thereby altering membrane permeability and internal homeostasis.
Method of Use of β-Defensin Polypeptides β-defensin peptides suitable for use in the methods and compositions of the present invention include natural β-defensin peptides isolated from known cellular sources, synthetic peptides produced by solid phase or recombinant DNA techniques, and β-defensin analogs which may be smaller peptides or other molecules having similar binding and biological activity as the natural defensin peptides.

The isolation and sequencing of natural β-defensin peptides are well described in the scientific and patent literature. In particular, such methods are described in Harder, et al., 1996, supra, and Zhoa, C., et al., 1996, supra, the disclosures of which are incorporated herein by reference. It will be appreciated that additional natural β-defensin peptides may be identified in the future from either the species listed or other species, which peptides will likely be useful in the methods and compositions of the present invention.

Minor modifications of the β-defensin primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the β-defensin still exists.

Synthetic peptides may also be used in the methods of the invention. Suitable synthetic peptides will usually comprise all or part of the amino acid sequence of a known peptide, more usually incorporating at least some of the conserved regions between human β-defensin 1 and human β-defensin 2.

In some cases, it may be desirable to incorporate one or more nonnatural amino acids in the synthetic β-defensin peptides of the present invention. Possible nonnatural amino acids will usually have at least an N-terminus and a C-terminus and will have side chains that are either identical to or chemically modified or substituted from a natural amino acid counterpart. An example of a nonnatural amino acid is an optical isomer of a naturally occurring L-amino acid. Examples of chemical modifications or substitutions include hydroxylation or chlorination of C—H bonds within natural amino acids. Such techniques are used in the manufacture of drug analogs of biological compounds and are known to one of ordinary skill in the art.

Synthetic peptides having biological and binding activity the same or similar to that of natural β-defensin peptides may be produced by either of two general approaches. First, the polypeptides may be produced by the well-known Merrifield solid-phase chemical synthesis method wherein amino acids are sequentially added to a growing chain. (See Merrifield, *J. Am. Chem. Soc.* 85:2149–2156, 1963.) Systems for manually synthesizing peptides on polyethylene pegs are available from Cambridge Research Biochemicals, Cambridge, Mass. Automatic peptide synthesis equipment is available from several commercial suppliers, including Applied Biosystems. Inc. Foster City, Calif.; Beckman Instruments, Inc., Waldwick, N.J.; and Biosearch, Inc., San Rafael, Calif. Using such automatic synthesizers according to manufacturer's instructions, peptides may be produced in quantities suitable for use in the present invention.

Second, the synthetic β-defensin peptides of the present invention may be synthesized by recombinant techniques involving the expression in cultured cells of recombinant DNA molecules encoding a gene for a desired portion of a natural or analog β-defensin molecule. The gene encoding the β-defensin peptide may itself be natural or synthetic. Conveniently, polynucleotides may be synthesized by well known techniques based on the desired amino acid sequence. For example, short single-stranded DNA fragments may be prepared by the phosphoramidite method described by Beaucage et al., *Tet. Lett* 22:1859–1862, 1981. A double-stranded fragment may then be obtained either by synthesizing the complementary strand and annealing the strands together under appropriate conditions or by adding the complementary strand using DNA polymerase under appropriate conditions or by adding the complementary strand using DNA polymerase with an appropriate primer sequence. The natural or synthetic DNA fragments coding for the desired β-defensin peptide may then be incorporated in a suitable DNA construct capable of introduction to and expression in an in vitro cell culture.

The methods and compositions of the present invention may also employ synthetic nonpeptide compositions that have biological activity functionally comparable to that of the known β-defensin peptides. By functionally comparable, it is meant that the shape, size, flexibility, and electronic configuration of the nonpeptide molecule is such that the biological activity of the molecule is similar to the a β-defensin peptide. In particular, the nonpeptide molecules should display comparable antimicrobial activity. Such nonpeptide molecules will typically be small molecules having a molecular weight in the range from about 100 to 1000 daltons. The use of such small molecules is frequently advantageous in the preparation of pharmacological compositions.

The identification of such nonpeptide analog molecules can be performed using techniques known in the art of drug design. Such techniques include, but are not limited to, self-consistent field (SCF) analysis, configuration interaction (CI) analysis, and normal mode dynamics computer analysis, all of which are well described in the scientific literature. (See, e.g., Rein et al., *Computer-Assisted Modeling of Receptor-Ligand Interactions*, Alan Liss, New York, 1989.) Preparation of the identified compounds will depend on the desired characteristics of the compounds and will involve standard chemical synthetic techniques. (See Cary et al., *Advanced Organic Chemistry*, part B, Plenum Press, New York, 1983.)

The term "substantially purified" as used herein refers to a polypeptide which is substantially free of other proteins, lipids, carbohydrates or other materials with which it is is naturally associated. One skilled in the art can purify β-defensin using standard techniques for protein purification. The substantially pure polypeptide will yield a single major band on a non-reducing polyacrylamide gel. The purity of the β-defensin polypeptide can also be determined by amino-terminal amino acid sequence analysis.

By "therapeutically effective amount" is meant the quantity of a compound according to the invention necessary to prevent, to cure or at least partially treat a wound in a subject. A subject is any mammal, preferably a human.

Wound healing is a complex and protracted process of tissue repair and remodeling involving many different cell types which requires a finely tuned control of various biochemical reaction cascades to balance the regenerative processes. Wound healing is generally divided into three phases: inflammation, proliferation, and maturation (Waldorf, H., and Fewkes, J., 1995, "Wound Healing," *Adv. Dermatol.* 10:77–96). In a wound, the size of an inoculum of microorganisms, the virulence of the organisms, and host antimicrobial defense mechanisms determine if an infection will develop. Thus, antibiotics and antimicrobial peptides can also be of therapeutic value in the treatment of wounds (Edlich, R. F., et al., 1986, "Antimicrobial treatment of minor soft tissue lacerations: a critical review," *Emergency Medical Clinics of North America* 4(3):561–80). Wounds can develop in any tissue, but are common in the skin and the eyes. In one embodiment, the method of the invention is used to treat a corneal epithelial wound.

In another embodiment, a method for treating a subject having or at risk of having a corneal infection, by administering a therapeutically effective amount of a β-defensin polypeptide, is provided. A subject is any mammal, preferably a human. The invention may be used to identify or treat individuals who are "at risk" of developing a corneal infection or a corneal wound. These individuals may be identified by a method of the invention for detecting the presence or absence of β-defensin or by any other diagnostic means. A subject may be treated by a method of the invention prior to the actual onset of the clinical appearance of infection. The "clinical appearance" can be any sign or symptom of the infection. Specific, non-limiting examples of a subject at risk of a corneal infection is a subject who wears contact lenses, a subject who has undergone surgery to the eye, or a subject who has undergone laser irradiation of the eye. The subject can be at risk of infection with the leading pathogen responsible for contact lens-associated vision threatening corneal disease, *Pseudomonas aeruginosa*, or any other pathogen.

In a further embodiment, compounds identified to affect the expression of a β-defensin can be used to treat a subject having or at risk of having a corneal wound or corneal infection. Treatment can include modulation of β-defensin gene expression and β-defensin activity by administration of a therapeutically effective amount of a reagent that modulates the β-defensin. The term "modulate" envisions the augmentation of the expression of β-defensin when it is under-expressed. Compounds that modulate β-defensin expression can be identified by a method of the invention (see below) or by any other means (e.g., transcriptional binding assays, etc.)

Method for Identifying Compounds Which Affect a β-Defensin

The invention provides a method for identifying a compound which can modulate a human β-defensin activity. The method includes incubating compounds with ocular epithelial cells, such as corneal cells, and measuring the effect of the compound on the expression or activity of β-defensin. By "expression" is meant the production or level of either β-defensin-2 mRNA or β-defensin-2 polypeptide. The activity of β-defensin in the sample can then be compared to the β-defensin activity of a control sample not incubated with the compound. The compounds which affect β-defensin include peptides, polypeptides, chemical compounds and biological agents.

"Incubating" includes conditions which allow contact between the test compound and the ocular cells. "Contacting" includes both solution and solid phase contact. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., 1985, *Bio/Technology*, 3:1008–1012), allele-specific oligonucleotide (ASO) probe analysis (Conner et al., 1983, *Proc. Natl. Acad. Sci. USA*, 80:278), oligonucleotide ligation assays (OLAs) (Landegren et al., 1988, *Science*, 241:1077), and the like. Molecular techniques for DNA analysis have been reviewed (Landegren et al., 1988, *Science*, 242:229–237).

A compound can affect β-defensin by either stimulating or inhibiting β-defensin. A compound "inhibits" β-defensin if the expression of β-defensin or any anti-microbial properties of the sample is decreased. A compound "stimulates"

β-defensin if the expression of β-defensin or any antimicrobial properties of the sample is increased.

The sample can be any sample of interest. The sample may be a cell sample or a membrane sample prepared from a cell sample. Suitable cells include any host cells containing a recombinant β-defensin vector of the invention or a primary culture of an ocular epithelial cell, such as a corneal cell expressing an endogenous β-defensin. Alternatively, cell lines expressing an endogenous β-defensin polypeptide can be used.

The effect of the compound on β-defensin can be measured by assessing the expression of β-defensin by methods well known in the art (e.g., Northern blots or polymerase chain reaction (PCR) analysis). Alternatively, the effect of the compound on the activity of β-defensin can be assessed.

Method of Use of β-Defensin Polynucleotides

The present invention also provides gene therapy for the treatment of disorders which are associated with β-defensin protein. Such therapy would achieve its therapeutic effect by introduction of a therapeutic polynucleotide into cells having the disorder.

The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxribonucleotides, or modified forms of either nucleotide. The term includes single and double forms of DNA. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of β-defensin polypeptide encoded by the nucleotide sequence is functionally unchanged.

The nucleotide sequence encoding the β-defensin polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

In the present invention, the β-defensin polynucleotide sequences may be inserted into an expression vector. The term "expression vector" refers to a plasmid, virus or other vehicle known in the art that has been manipulated by insertion or incorporation of the β-defensin genetic sequences. Polynucleotide sequence which encode β-defensin can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). Promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding β-defensin may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells.

The "therapeutic polynucleotide" may be polynucleotide sequences encoding β-defensin, or polynucleotide sequences which encode a gene which regulates β-defensin. Delivery of the therapeutic polynucleotide can be achieved using a recombinant expression vector such as a chimeric virus or a colloidal dispersion system. Especially preferred for therapeutic delivery of β-defensin polynucleotides is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes.

All of these vectors can transfer or incorporate a gene for a selectable marker so that transduced cells can be identified and generated. By inserting a β-defensin sequence of interest into the viral vector, along with another gene which encodes the sequence for a receptor on a specific target cell, for example, the vector is now target specific. Retroviral vectors can be made target specific by attaching, for example a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the β-defensin polynucleotide.

Since recombinant retroviruses are defective, they require assistance in order to produce infectious vector particles. This assistance can be provided, for example, by using helper cell lines that contain plasmid encoding all of the structural genes of the retrovirus under the control of regulatory sequences within the LTR. These plasmid are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmid encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.*, 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., 1988, *Biotechniques*, 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Pharmaceutical Compositions

This invention further provides a composition for administering to a subject having or at risk of having a corneal wound or infection a therapeutically effective dose of a β-defensin in a pharmaceutically acceptable carrier. "Administering" the pharmaceutical composition of the present invention may be accomplished by any means known to the skilled artisan. The pharmaceutical compositions according to the invention are in general administered topically, but other routes of administration, such as intradermal or intravenous injection, can also be utilized.

The compositions of the present invention comprise β-defensin polypeptides-2 incorporated in a physiologically acceptable carrier suitable for topical application to the affected area. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition and animal models may be used to determine effective dosages for treatment of particular disorders. Various considerations are described, e.g., in Gilman et al., eds., 1990. Goodman And Gilman's: The Pharmacological Bases of Therapeutics, 8th ed., Pergamon Press; and Remington's Pharmaceutical Sciences, 1990, 17th ed., Mack Publishing Co., Easton, Pa., each of which is herein incorporated by reference.

In general, the compositions may contain from about 0.1 nM to 10 mM β-defensin polypeptide, usually containing from about 0.01 μM 1 mM β-defensin polypeptide, and more usually containing from about 0.1 μM to 100 μM β-defensin polypeptide. Under certain circumstances, however, higher or lower doses may be appropriate. The administration of the dose can be carried out both by single administration in the form of an individual dose unit or else several smaller dose units and also by multiple administration of subdivided doses at specific intervals.

The nature of the carrier will vary depending on the intended area of application. For application to the skin, a cream or an ointment base is usually preferred, with suitable bases including lanolin, silver sulfadiazine, also known as SILVERDENE™ (Duke Laboratories, South Norwalk, Conn.), and the like. It will also be possible to incorporate the β-defensin polypeptides in natural and synthetic bandages and other wound dressings to provide for continuous exposure of a wound to the peptide. Aerosol applicators may also find use. It is also possible that β-defensins will be incorporated in or coated on implantable devices, such as heart pacemakers, intralumenal stents, and the like where both the anti-microbial and growth promoting activity will be of benefit. Coating may be achieved by nonspecific adsorption or covalent attachment.

For corneal treatment, the carrier will be suitable for application to the eyes. Preparation of suitable ophthalmic solutions requires careful consideration of factors such as isotonicity, the need for buffering agents, the need for preservatives, and sterilization. Lacrimal fluid is istonic with blood, having an isotonicity value corresponding to that of a 0.9% sodium chloride solution. Ideally, an ophthalmic solution should have this isotonicity value, but eyes can tolerate isotonicity values as low as that of a 0.6% sodium chloride solution and as high as that of a 2.0% solution without substantial discomfort. Some ophthalmic solutions are necessarily hypertonic in order to enhance absorption and provide a concentration of the active peptide strong enough to exert a prompt and effective action. Suitable ophthalmic carriers include ointments, saline solutions, isotonic saline solution, such as SORBI-CARE™ (Allergan Pharmaceuticals), ointments such as NEODECADRONE™ (dexamethasanephosphate 0.1% and neomycin sulfate 0.5%) (Merck, Sharp, and Dhome) and the like. Suitable ointment bases are sold under the tradename LACRI-LUBE™ (Allergan), a lubricating tear ointment.

Other suitable ophthalmic vehicles include boric acid which has a pH slightly below 5.0. Phosphate buffer system may also be employed and adjusted for isotonicity may provide a choice of pH ranging from about 5.9 to 8.0. Pharmaceutical grade of methyl cellulose may also be employed having a variable viscosity.

In addition to β-defensin peptides, the compositions of the present invention may include other known growth factors, such as epidermal growth factor, platelet-derived growth factor, insulin-like growth factor, transforming growth factor-β fibroblast growth factor, and the like.

The β-defensin compositions of the present invention will be useful for treating a wide variety of wounds affecting virtually any tissues of the body. In particular, the compositions will be useful for treating cutaneous wounds affecting the epidermal and dermal layers of the skin, as well as injuries to the cornea and epithelial-lined hollow organs. The wounds may be caused by a wide variety of physical trauma, including cuts, abrasions, burns, chemical exposure, and the like, as well as from surgical procedures, such as surgical incisions and skin grafting. The wounds may also result from disease including chronic conditions, such as a venous stasis ulcers, diabetic ulcers, and other nonhealing (trophic) conditions.

The β-defensin compositions of the present invention will find particular use in treating corneal and scleral wounds, including wounds which affect the epithelial layer, stromal layer and endothelial layers of the eye. For use in wound treatment, the β-defensin compositions will usually have a concentration in the range described above. The β-defensin compositions will usually be applied to the affected area periodically, typically from about 1 to 12 times each day, usually over a period of from about 3 to 14 days, depending on the nature of the wound. In some cases, it may be desirable to apply the compositions indefinitely. The β-defensin compositions still find particular use in the treatment of wound resulting form surgery and other intentional interventions where the compositions may be applied immediately after completion of the surgery.

In addition to the treatment of wounds, the β-defensin compositions of the present invention are particularly suitable for the treatment of microbial-related infections and diseases, particularly dermal infections, microbial-mediated dental disease, and ocular diseases such as microbial keratitis. For use in the treatment of such microbial infections, the compositions preferably employ a β-defensin concentration in the range set forth above. The compositions will typically be applied periodically, usually from about 1 to 12 times each day, for a period which may range from 3 to 21 days. For the treatment of dental disease, the compositions should be applied at least daily for an unlimited period.

The β-defensins will find particular use as a component int he solutions used for storage and transfer of corneas prior to transplant. The β-defensin concentration will be in the broad range set forth above. The β-defensins can act as both an antimicrobial agent both before and after the cornea has been transplanted.

Another aspect of the invention is a formulation comprising a β-defensin-2 inducing compound, and a pharmaceutically acceptable excipient. Such compounds may be formulated as described above. The dosage necessary to effect expression of a therapeutic amount of β-defensin-2 will vary depending on the potency of the compound selected, but may be determined following the assays and examples described herein.

Thus the identification of β-defensin provides a useful tool for diagnosis, prognosis and therapeutic strategies associated with expression of β-defensin.

EXAMPLE 1

In order to determine if the human corneal epithelium may avoid opportunistic infection by producing its own endogenous anti-microbial substances when exposed to potential pathogens, the expression of human β-defensin-2 in human corneal epithelium was examined. To determine if anti-microbial peptides were expressed by human corneal epithelium, human epithelial cells were maintained in supplemental hormonal epitheial medium containing 15% fetal bovine serum. After 5 to 7 days, when plates were tightly packed with polygonal cells, mRNA was extracted using an mRNA isolating kit known as the RNA MINIPREP KIT™ (Quiagen). The mRNA was then converted to cDNA by placing 500 ng of RNA sample into a master mix containing 5× buffer, 10 mM dNTPs, Rnase inhibitor, superscript reverse transcriptase (Rtase), random primer, DTT, DEPC water (final vol. 20 μl). Samples were incubated for 1 hour at 42° C., and then for 15 mm at 95° C. (to denature RTase), and target cDNA was then selectively amplified using polymerase chain reaction (PCR). The reaction mixture included 20 mM 5' and 3' custom hBD-2 primers (Life Technologies Inc.) 10 mM each dNTP, 10×PCR buffer, and 1.25 U of *Thermus aquaticus* polymerase in a total volume of 50 µl. Each cycle included denaturation at 94 C for 50 seconds, annealing of primer to cDNA template at 55 C for 1 min, and primer extension at 72 C for 1 min. The PCR products were analyzed by agarose gel electrophoresis with ethidium bromide staining and the amplified DNA band was extracted from the gel and sequenced. Sequencing was conducted using dye termination chemistry and *Thermus aquaticus* polymerase, such as the AMPLI-TAQ™ (Perkin-Elmer Applied Biosystems) reaction mixture following the manufacturer's recommended protocol.

Using RT-PCR, the primers amplified a 257 bp sequence from human corneal epithelial cell cDNA. The amino acid sequence of this DNA band was computer-matched with the known cDNA sequence of hBD-2 available from EMBL/ Genbank database, accession number Z71389. These results showed expression of that hBD-2 mRNA by cultured human corneal epithelial cells.

The results suggest that:

1. hBD-2, or factors that upregulate the production of hBD-2, can be used as a therapeutic agent for preventing and/or treating infectious keratitis associated with the use of contact lenses.

2. hBD-2, or factors that upregulate the production of hBD-2, can be used as a therapeutic agent for preventing and/or treating other bacterial infections of the ocular tissues.

3. hBD-2, or factors that upregulate the production of hBD-2, can be used as a therapeutic agent for preventing and/or treating *P. aeruginosa* infection in other sides of the body, e.g., pneumonia, burn/wound and other skin infections.

4. hBD-2, or factors that upregulate the production of hBD-2, can be used as a therapeutic agent for preventing and/or treating bacterial infections in other sites of the body.

EXAMPLE 2

Corneal epithelial cells were maintained in supplemental hormonal epithelial medium containing 15% fetal bovine serum. After 4 to 6 days, when the plates were tightly packed with polygonal cells, a *P. aeruginosa* conditioned medium or a control medium was applied to the epithelial cells. Conditioned medium was be prepared as follows: *P. aeruginosa* strains PAO1 (Fisher IT-7, parent strain) and AK1012 (LPS mutant) were grown in M9 medium with aeration at 37° C. to late long phase (Li, J. D., et al., "Transcriptional activation of mucin by *Pseudomonas aeruginosa* lipopolysaccharide in the pathogenesis of cystic fibrosis lung disease," Proc. Natl. Acad. Sci. USA 94, 1997). AK1012 is an LPS-rough mutant derived from PAO1 by its resistance to lysis by the O side chain-specific bacteriophage E79. The broth cultures were then centrifuged at 10,000 rpm for 50 minutes, and the supernatants containing bacterial exoproducts were passed through a 0.22 µ filter for sterilization. Bacterial culture supernatants were added to epithelial culture medium at a 1:4 dilution and were incubated at 37° C. for six hours with the corneal epithelial cells. Control cells were incubated with a 1:4 dilution of M9 media in cell culture medium. After the six hour incubation, human β-defensin-2 mRNA expression was measured by reverse transcription polymerase chain reaction (RT-PCR). The intensity of the amplified bands was analyzed using the program "NIH Image," version 6.1.

The primers amplified a 257 base pair sequence from human corneal epithelial cell cDNA produced from cells stimulated with either PAO1 or AK1012 conditioned media, or the control medium. Upregulation of human β-defensin-2 mRNA expression occurred only in human cornea cells treated with *P. aeruginosa* strain PAO1 conditioned medium. A GAPDH standard was used to standardize the total amount of cDNA present in each PCR reaction. The mean density of the human β-defensin-2 cDNA band in corneal cells stimulated with the strain PAO1 conditioned media was 197.3, which was substantially greater than the mean density of 85.13 detected for the human β-defensin-2 cDNA band from corneal cells stimulated with AK1012, or the mean density of 69.25 detected for the human β-defensin-2 cDNA band from control cells.

The results suggest that *P. aeruginosa* LPS is responsible for upregulation of human β-defensin-2 mRNA expression in corneal epithelial cells treated with *P. aeruginosa*. LPS is a major virulence factor for *P. aeruginosa* and is the major target antigen for protective antibodies arising in response to acute infection and vaccination (Cryz, S., et al., Infect Immun. 40:659–664, 1983; Cryz, S., et al., J. Lab. Clin. Med. 111:701–707, 1988). The LPS defective strain AK1012 produces an LPS with a of a trucated core, and further has the loss of O side chain synthesis. The lack of upregulation of human β-defensin-2 by strain AK1012 as compared to the parent strain PAO1 suggests that bacterial LPS is responsible for up-regulation of the transcription of human β-defensin-2 in *P. aerliginosa* exposed corneal epithelium. Since the defect in AK1012 does not involve endotoxin, it suggests that endotoxin itself is not involved in upregulation of human β-defensin-2 in *P. aeruginosa* exposed corneal epithelium. Stimulation of endogenous human β-defensin-2 using a portion of the LPS molecule that activates human β-defensin transcription may provide an ideal therapeutic agent or tear film supplement to prevent or treat the occurrence of corneal infection.

What is claimed is:

1. A method of treating a subject having or at risk of having a corneal wound or a corneal infection, the method comprising:

contacting corneal cells of the subject with a sufficient amount of a compound which is a bacterial lipopolysaccharide or a portion thereof to modify expression or activity of endogenous β-defensin.

2. The method of claim 1, wherein the bacterial lipopolysaccharide is administered in an amount sufficient to improve the condition of the wound or infection.

3. The method of claim 1, wherein the bacterial lipopolysaccharide is lipopolysaccharide from *Pseudomonas aeruginosa*.

4. The method of claim 3 wherein the *Pseudomonas aeruginosa* is strain PAO1.

* * * * *